(12) United States Patent
Tang et al.

(10) Patent No.: US 10,825,210 B2
(45) Date of Patent: Nov. 3, 2020

(54) METHOD AND APPARATUS FOR PROJECTION DOMAIN TRUNCATION CORRECTION IN COMPUTED-TOMOGRAPHY (CT)

(71) Applicants: CANON MEDICAL SYSTEMS CORPORATION, Otawara-shi (JP); THE UNIVERSITY OF CENTRAL FLORIDA RESEARCH FOUNDATION, Inc., Orlando, FL (US)

(72) Inventors: Qiulin Tang, Buffalo Grove, IL (US); Alexander Katsevich, Oviedo, FL (US); Zhou Yu, Wilmette, IL (US); Wenli Wang, Briarcliff Manor, NY (US)

(73) Assignees: CANON MEDICAL SYSTEMS CORPORATION, Otawara-shi (JP); THE UNIVERSITY OF CENTRAL FLORIDA RESEARCH FOUNDATION, Inc., Orlando, FL (US)

( * ) Notice: Subject to any disclaimer, the term of this patent is extended or adjusted under 35 U.S.C. 154(b) by 136 days.

(21) Appl. No.: 16/206,892

(22) Filed: Nov. 30, 2018

(65) Prior Publication Data

US 2019/0164317 A1   May 30, 2019

Related U.S. Application Data

(60) Provisional application No. 62/592,987, filed on Nov. 30, 2017.

(51) Int. Cl.
*G06T 5/00* (2006.01)
*G06T 11/00* (2006.01)
(Continued)

(52) U.S. Cl.
CPC ............ *G06T 11/006* (2013.01); *A61B 6/032* (2013.01); *A61B 6/035* (2013.01); *A61B 6/5205* (2013.01);
(Continued)

(58) Field of Classification Search
CPC ......... G06T 11/006; G06T 5/002; G06T 5/20; G06T 2207/10081; G06T 2207/20182;
(Continued)

(56) References Cited

U.S. PATENT DOCUMENTS 6,307,909 B1   10/2001   Flohr et al.
7,050,528 B2   5/2006    Chen
(Continued)

OTHER PUBLICATIONS

J. Hsieh, et al. "A novel reconstruction algorithm to extend the CT scan filed-of-view" Medical Physics 31, 2385 (2004), http://dx.doi.org/10.1118/1.1776673.
(Continued)

*Primary Examiner* — Ping Y Hsieh
(74) *Attorney, Agent, or Firm* — Oblon, McClelland, Maier & Neustadt, L.L.P.

(57) ABSTRACT

An apparatus and method are provided for computed tomography (CT) imaging to reduce truncation artifacts due to a part of an imaged object being outside the scanner field of view (FOV) for at least some views of a CT scan. After initial determining extrapolation widths to extend the projection data to fill a truncation region, the extrapolation widths are combined into a padding map and smoothed to improve uniformity and remove jagged edges. Then a hybrid material model fits the measured projection data nearest the truncation region to extrapolate projection data filling the truncation region. Smoothing the padding map is improved by the insight that in general smaller extrapolation widths are more accurate and trustworthy. Further, practical applications often include multiple inhomogeneous materials.

(Continued)

Thus, the hybrid material model provides a better approximation than single material models, and more accurate fitting is achieved.

20 Claims, 12 Drawing Sheets

(51) Int. Cl.
*G06T 5/20* (2006.01)
*A61B 6/03* (2006.01)
*A61B 6/00* (2006.01)

(52) U.S. Cl.
CPC ............ *A61B 6/5282* (2013.01); *A61B 6/583* (2013.01); *G06T 5/002* (2013.01); *G06T 5/20* (2013.01); *A61B 6/4441* (2013.01); *G06T 2207/10081* (2013.01); *G06T 2207/20182* (2013.01); *G06T 2207/20192* (2013.01); *G06T 2207/30004* (2013.01); *G06T 2211/421* (2013.01); *G06T 2211/424* (2013.01); *G06T 2211/432* (2013.01)

(58) Field of Classification Search
CPC . G06T 2207/20192; G06T 2207/30004; G06T 2211/421; G06T 2211/424; G06T 2211/432; A61B 6/032; A61B 6/035; A61B 6/5205; A61B 6/5282; A61B 6/583; A61B 6/4441
See application file for complete search history.

(56) References Cited

U.S. PATENT DOCUMENTS

| 7,660,380 | B2 | 2/2010 | Boese et al. |
| 2004/0030246 | A1 | 2/2004 | Townsend et al. |
| 2008/0165918 | A1 | 7/2008 | Scholz |
| 2013/0004045 | A1 | 1/2013 | Dennerlein |
| 2015/0029178 | A1 | 1/2015 | Claus et al. |
| 2017/0086767 | A1* | 3/2017 | Elsasser ............... A61B 6/5205 |
| 2018/0114325 | A1* | 4/2018 | Sanders .................. G06T 5/40 |
| 2018/0125438 | A1* | 5/2018 | Lauritsch ............. A61B 6/4014 |
| 2018/0211420 | A1* | 7/2018 | Yoo ........................ G06T 5/003 |
| 2019/0076101 | A1* | 3/2019 | Pan ........................ A61B 6/032 |

OTHER PUBLICATIONS

R. Clackdoyle, et al. "Data consistency conditions for truncated fanbeam and parallel projections", Med Phys, 42(2), pp. 831-845 (2015).

Yiheng Zhang, et al., "Artifact Reduction Methods for Truncated Projections in Iterative Breast Tomosynthesis Reconstruction", NIH Public Access, J Comput Assist Tomogr. Author Manuscript, available in PMC Sep. 15, 2009.

* cited by examiner

METHOD AND APPARATUS FOR PROJECTION DOMAIN TRUNCATION CORRECTION IN COMPUTED-TOMOGRAPHY (CT)

CROSS-REFERENCE TO RELATED APPLICATIONS

This application is based upon and claims the benefit of priority to provisional U.S. Application No. 62/592,987, filed Nov. 30, 2017, the entire contents of which are incorporated herein by reference.

FIELD

The illustrative embodiments described herein relate to correcting for truncation in computed tomography (CT), and, more particularly, to extrapolating X-ray attenuation values for virtual pixels extending beyond an edge of an array of X-ray detector elements.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body substantially in the projection plane. The attenuation of the radiation that has passed through the body is measured by processing electrical signals received from the detector.

Making projective measurements at a series of different projection angles through the body, a sinogram can be constructed from the projection data, with the spatial dimension of the detector array along one axis (e.g., the vertical axis) and the projection angle dimension along the other axis (e.g., the horizontal axis). For a CT scan using parallel X-rays, each volume within the body projects in the sinogram to respective sine waves with a period of one completer rotation and centered at the rotation axis (i.e., the isocenter of the CT scan). In cylindrical coordinates with respect to the rotation axis, the amplitude of the sinewave corresponds to distance from the rotation axis, and the phase corresponds to the angular position around the rotation axis.

In view of the unique mapping between volumes within the body and sine waves in the projection data, a three-dimension image of the body can be reconstructed from two-dimensional projection data by performing an inverse Radon transform (or using any other image known reconstruction method). Similarly, a two-dimensional image of a cross-section of the body can be reconstructed from a sinogram of one-dimensional projections through the cross-section of the body. In general, the image reconstruction problem can be solved using any of several methods including: back-projection methods (e.g., filtered back-projection), iterative reconstruction methods (e.g., the algebraic reconstruction technique (ART) method and the total variation minimization regularization methods), Fourier-transform-based methods (e.g., direct Fourier method), and statistical methods (e.g., maximum-likelihood expectation-maximization algorithm based methods).

Often the image reconstruction problem will be formulated as a matrix equation $$Ax=p,$$

where p are the projection measurements of the X-rays transmitted through an object space that includes the object OBJ, A is the system matrix describing the discretized line integrals (i.e., the Radon transforms) of the X-rays through the object space, and x is the image of object OBJ (i.e., the quantity to be solved for by solving the system matrix equation). The image x is a map of the attenuation as a function of position. The image x can be reconstructed from the projection data p using one of many reconstruction methods, including, a filtered-back-projection (FBP) method, a Feldkamp-Davis-Kress (FDK) method, and an iterative reconstruction (IR) method. Unfortunately, a reconstructed image can include artifacts degrading the image when the field of view (FOV) of the X-ray beam subtends a solid angle that is too small to completely cover the object OBJ being imaged. In this case, incomplete information exists for the portions of the object outside of the FOV of the X-ray beam, and the image quality of the reconstructed image will depend on how this incomplete information it treated. The same problem also manifests when the projection FOV is limited by the size of an X-ray detector rather the size of the X-ray beam, such as when a flat panel detector is too small to capture an entire X-ray beam and the wings of the X-ray beam spill over the edges of the flat panel detector (or would spill over the edges of the flat panel detector except for an aperture filter provided to limit X-ray exposure and keep the dose as low as reasonably possible).

Accordingly, methods of accounting for the incomplete information of truncated projection data are desired to mitigate truncation effects and preserve good image quality even when the projection FOV is smaller than the imaged object OBJ.

BRIEF DESCRIPTION OF THE DRAWINGS

A more complete appreciation of the disclosed inventions and the many attendant advantages thereof will be readily obtained as the same becomes better understood by reference to the following detailed description when considered in connection with the accompanying drawings, wherein.

DETAILED DESCRIPTION

The above discussed situation in which a field of view (FOV) for projection data is too narrow to span an imaged object is not uncommon. In a computed tomography (CT) scanner, the term "FOV" means the volume traced by X-rays from the X-ray source to the detector of those X-ray trajectories—excluding scatter—that generate projection data (e.g., the solid angle subtended by the X-ray beam, assuming that the X-ray beam does not overfill the detector). For example, C-arm cone-beam CT (CBCT) has been used increasingly as an imaging tool in surgical suites. CBCT has the benefit of rapidly providing detailed 3D anatomical information. Further, CBCT can also be used generate images with high-spatial resolution, and, therefore, C-arm CBCT has been widely used in numerous imaging applications of high-contrast structures such as the sinuses, teeth, spines and contrast-enhanced vasculatures. However, in conventional analytical image reconstruction, soft-tissue imaging using C-arm CBCT remains challenging due to degradation of low-contrast features resulting from truncation artifacts. These truncation artifacts arise because conventional CBCT systems have a limited FOV.

The methods and apparatus described herein reduce the above-discussed artifacts by virtually expanding the projection data to include virtual projection data representing X-ray attenuation values beyond the edges of the measured attenuation values within the detector array. The virtual projection data are extrapolated from the measured attenuation values according to assumed properties/characteristics of the imaged object.

Figure 1A:
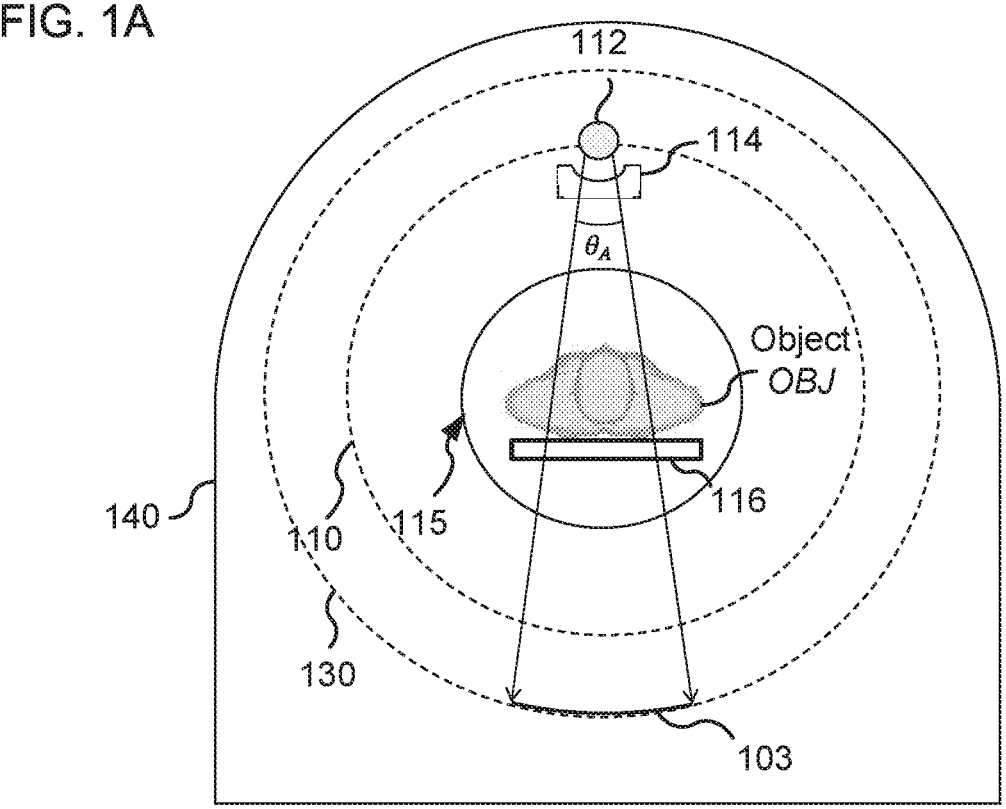
FIG. 1A shows a diagram of a first orientation of a computed tomography (CT) scanner in which an imaged object is within a scanner field of view (FOV), according to one implementation.
Figure 1B:
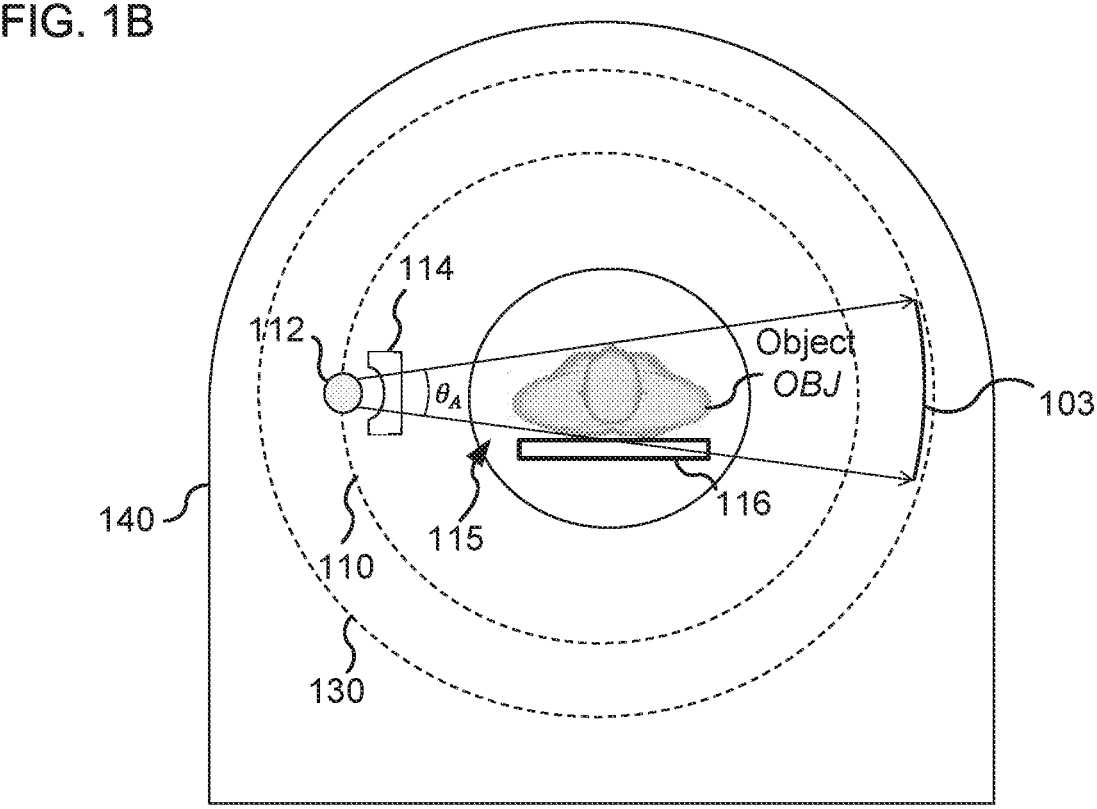
FIG. 1B shows a diagram of a second orientation of the CT scanner in which an imaged object extends outside of the scanner FOV, according to one implementation.
Figure 2:
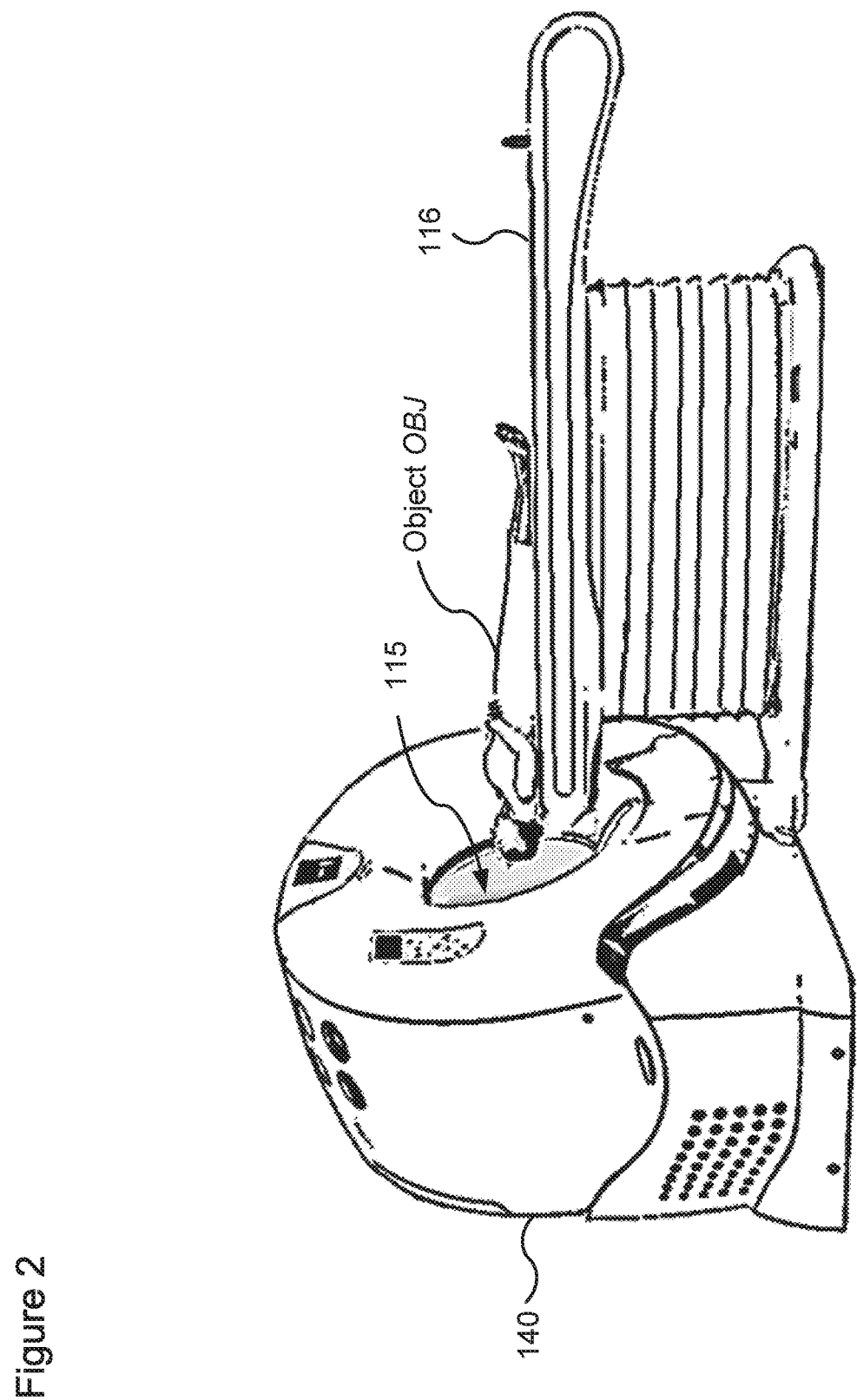
FIG. 2 shows a drawing of a non-portable CT scanner, according to one implementation.

Referring now to the drawings, wherein like reference numerals designate identical or corresponding parts throughout the several views, FIGS. 1A and 1B show a schematic diagram of source and detector portions of a computed tomography (CT) scanner having an array energy-integrating detectors arranged in a third-generation geometry. The diagram illustrates relative positions among an object OBJ to be scanned resting on a table 116, an X-ray source 112, a collimator/filter 114, and an X-ray detector 103. FIG. 2 shows a drawing of the CT scanner, and, although the CT scanner is representative of larger CT scanners than the portable CBCT systems discussed above, the issues with truncation artifacts can occur in any scanner if the scanner FOV fails to complete span the attenuating objects within the FOV, including the object OBJ and the table 116.

In one implementation, the X-ray source 112, the collimator/filter 114 are fixedly connected to a rotational component 110 that is rotatably connected to a gantry 140. The gantry 140 of the CT scanner also includes an open aperture 115 enabling the object OBJ to be placed in a projection plane of the X-rays from the X-ray source 112. The X-ray detector 103 is fixedly connected to a rotational component 130 that is rotatably connected to the gantry 140. The rotational component 120 and the rotational component 130 can rotate in unison maintaining the X-ray detector 103 in a position diametrical opposed to the X-ray source 112 to obtain projection data of the object OBJ at a progression of projection angles (also referred to as views). As discussed above in the Background Section, sinograms are created by arranging the projection data with projection angles arranged along one axis and the spatial dimensions of the projection data arranged along the other axes.

FIG. 1A shows a first view in which the object OBJ, which is oblong, is irradiated along its short axis, and projection data for only the center of the object OBJ (e.g., the shoulder and arms of a patient are truncated in the projection data). In contrast, FIG. 1B shows a second view in which the X-ray source 112 and X-ray detector 103 have been rotated 90° from the first view and the object OBJ is irradiated along its long axis. In this second view the object OBJ is entirely represented in the projection data, but the table 116, which also attenuates the X-rays is not completely represented in the projection data for the second view.

Figure 3:
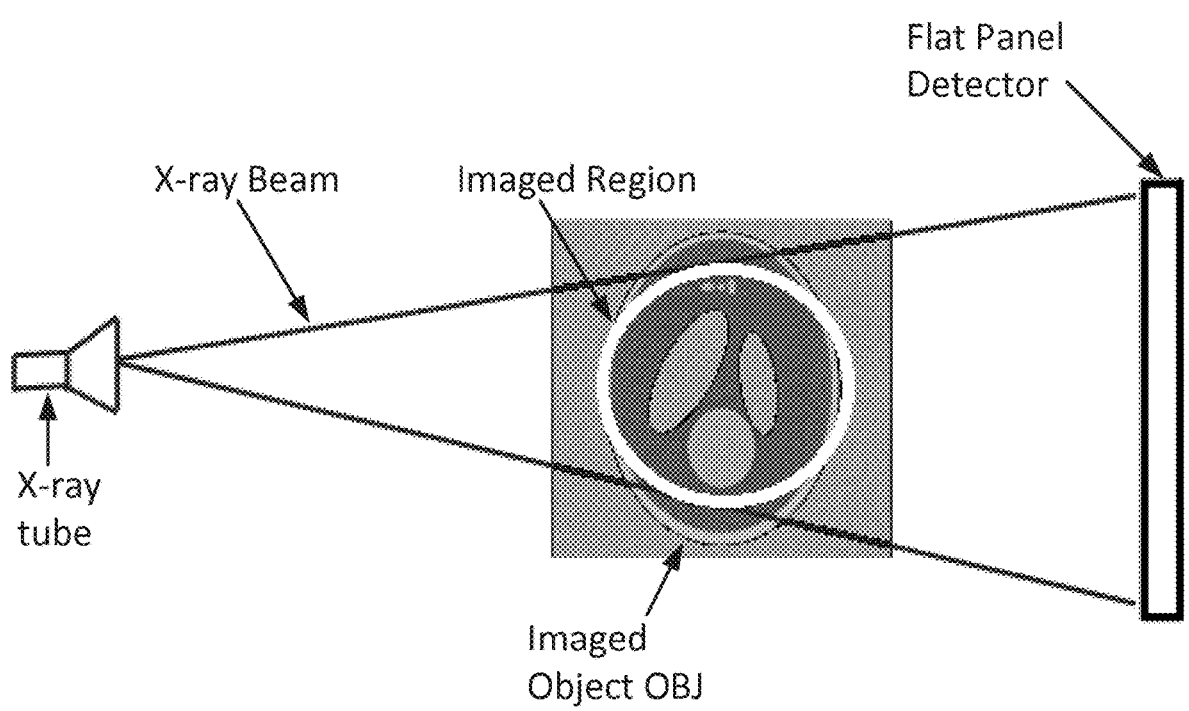
FIG. 3 shows a diagram of a portable C-arm CT scanner using a flat panel detector in which an imaged object extends outside of the scanner FOV, according to one implementation.

Similarly, FIG. 3 illustrates another non-limiting example of the truncation effect, occurring in this example in a C-arm CBCT scanner using a flat panel detector (FPD). As mentioned above, CBCT is increasingly being used for imaging and guidance during interventional and surgical procedures. However, measured CBCT data are truncated often due to the limited detector size resulting in truncations artifacts, and these artifacts can obscure features in the reconstructed image. In FIG. 3, the imaged volume, which is a volume that is inside the FOV for all views, is smaller than the imaged object OBJ. Using a small image volume can have advantages for portability, higher resolution, faster image reconstruction, and decreasing radiation dosage, but using a smaller FDP and the commensurately smaller image volumes also creates a potential for truncation artifacts in a reconstructed image due to the attenuation of the projection data arising from portions of the object OBJ outside of the imaged volume. Thus, the smaller size of the FDP can result in data truncation during data acquisition for three-dimensional reconstruction.

The truncation artifact can be better understood by considering that, for some projection angles, the acquisition FOV fails to completely span the object OBJ, such that data that would make it possible to perfectly characterize the object OBJ is missing due to the limited extent of the FDP. The missed data will reduce the amount of known projection data p available to reconstruct the image based on the system-matrix equation $Ax \approx p$. When the FOV includes less than the entire object OBJ, the system-matrix equation tends to be underdetermined. That is, as a result of the system-matrix being modeled using a forward projection A, the image inside the FOV is more constrained by the equations than the image outside FOV, resulting in artifacts in the reconstructed image. Thus, truncation artifacts can manifest regardless of whether the image is reconstructed using IR methods or using FBP and FDK methods.

To remedy the problems of truncation of the projection data, the methods described herein virtually extend the projection data by extrapolating based on the measured projection data additional attenuation values for regions extending beyond the edge of the detector. Further, the methods described herein improve over other methods of extrapolation that either have limited applicability (e.g., they only work for parallel or fan beams but are incompatible with cone beams) or result in a jagged edge in the axial image as described below.

For example, truncation artifacts can be reduced using data consistency, as described in U.S. Pat. No. 7,050,528, incorporated herein by reference in its entirety. However, methods using data consistency are limited to two-dimensional scans, such as parallel-beam and fan-beam scans, and, therefore, are not applicable to most clinical CT scanner configurations.

Other methods (e.g., those in U.S. Pat. Nos. 6,307,909 and 7,660,380, which are both incorporated herein by reference in their entirety) that perform extrapolation using a row-by-row fit of the measured data suffer from accuracy problems and are susceptible to the undesirable effect of generating a jagged edge in the axial image.

In general, other methods of extending projection data through row-by-row extrapolation are prone to inaccuracy, without the additional measures of the methods described herein. For example, methods that, for each detector row, uses a polynomial fit of the of whole detector row to extend the projection data into the truncated region are prone to overlook the local trends (e.g., slope and curvature) in the projection data immediately adjacent to the truncation region while overemphasizing structure in the projection data far from the truncation region. Relatedly, in methods using a hypothetical water cylinder to fit and extend the projection data into truncated region, the accuracy of the extrapolation is degraded by assumptions regarding noise and material composition. Further, this degradation of the accuracy leads to an artificial effect of a jagged for the extended projection data in the truncation region. To mitigate the effects of noise in the projection data, a one-dimensional filter can be applied to the respective rows of the projection data before extrapolating. However, this only partly reduces the jagged edge. The methods provided herein go much farther towards eliminating the jagged edge for the extrapolated projection data (i.e., virtual attenuation values) extending into the truncated regions. Table 1 summarizes the above discussion contrasting advantages of method 200, which is a non-limiting example of the methods described herein, with other methods of extrapolation, as discussed above. Only method 200 is both compatible with three-dimensional reconstruction while generating extrapolated projection data in the truncation region without jagged edges in either the trans-axial or the axial image directions and without requiring material assumptions. The jagged edges in the trans-axial or the axial image directions is explained below with reference to FIGS. 4A and 4B.

TABLE 1

Comparison of extrapolation methods to extend projection data into truncation regions.

| Method | 2D/3D recon | Jagged edge in trans-axial image | Jagged edge in axial image | Matter. assum. needed |
|---|---|---|---|---|
| Data consistency | 2D | Not available | No | No |
| Global fitting | 2D/3D | No | Yes | Yes |
| Water fitting | 2D/3D | Yes | Yes | Yes |
| Smoothed extrapolation | 2D/3D | No | Yes | Yes |
| Method 200 | 2D/3D | No | No | No |

Figure 4A:
FIG. 4A shows a projection image in which the imaged object is truncated on the left side.
Figure 4B:
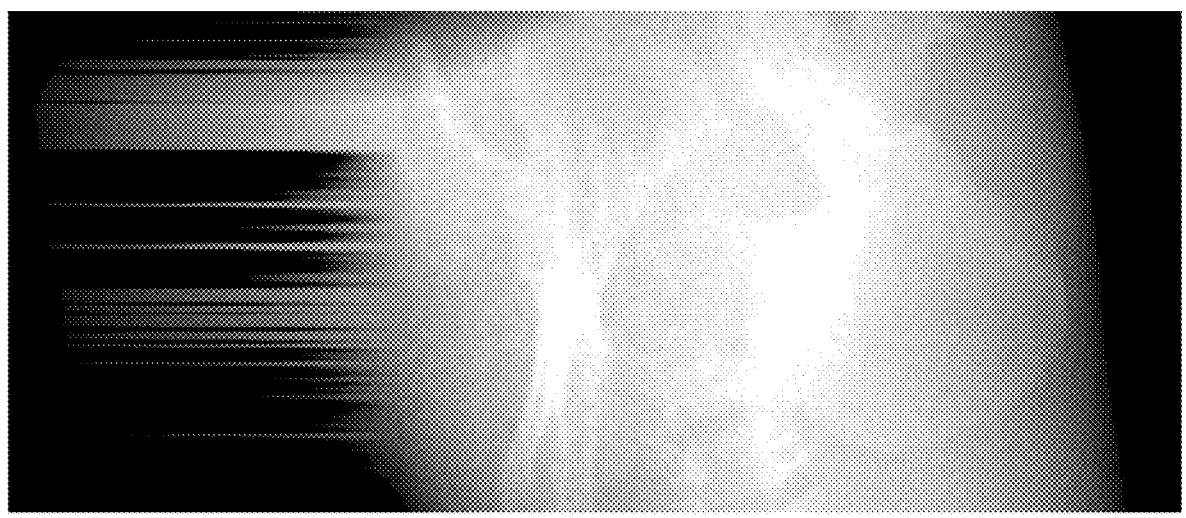
FIG. 4B shows a projection image in which a truncation region of the image in FIG. 4A has been filled using an extrapolation method that results in a jagged edge, according to one implementation.

FIG. 4A shows and example of projection data for which the imaged object is abruptly truncated at the left edge. Further, the type of material at the truncation boundary varies as a function of position along the left boundary, with bone represented toward the tope, muscle in the middle and skin at the bottom. FIG. 4B shows an extrapolation into the truncation region that results when the methods described herein are not used. For example, FIG. 4B shows that noise in the projection image leads to projection data that is non-smooth along view direction and has a jagged edge in the axial image. Further, the previous method used in generating FIG. 4B assumes a uniform material. That is, the difference of tissue types in truncation region is not addressed, and the effect of different material types can be even more significant in cases of severe truncation. In FIG. 4B, it can be observed that the effect of different tissue types is in addition to and different in kind than the effects of the noise. First, the effect of the different material types is much larger scale than the noise effect. Second, the different material types lead to low frequency protrusion and drop-well structures, rather than the of broad-band stochastic jagged structure (i.e., includes high-frequency components) resulting from the noise.

Figure 5:
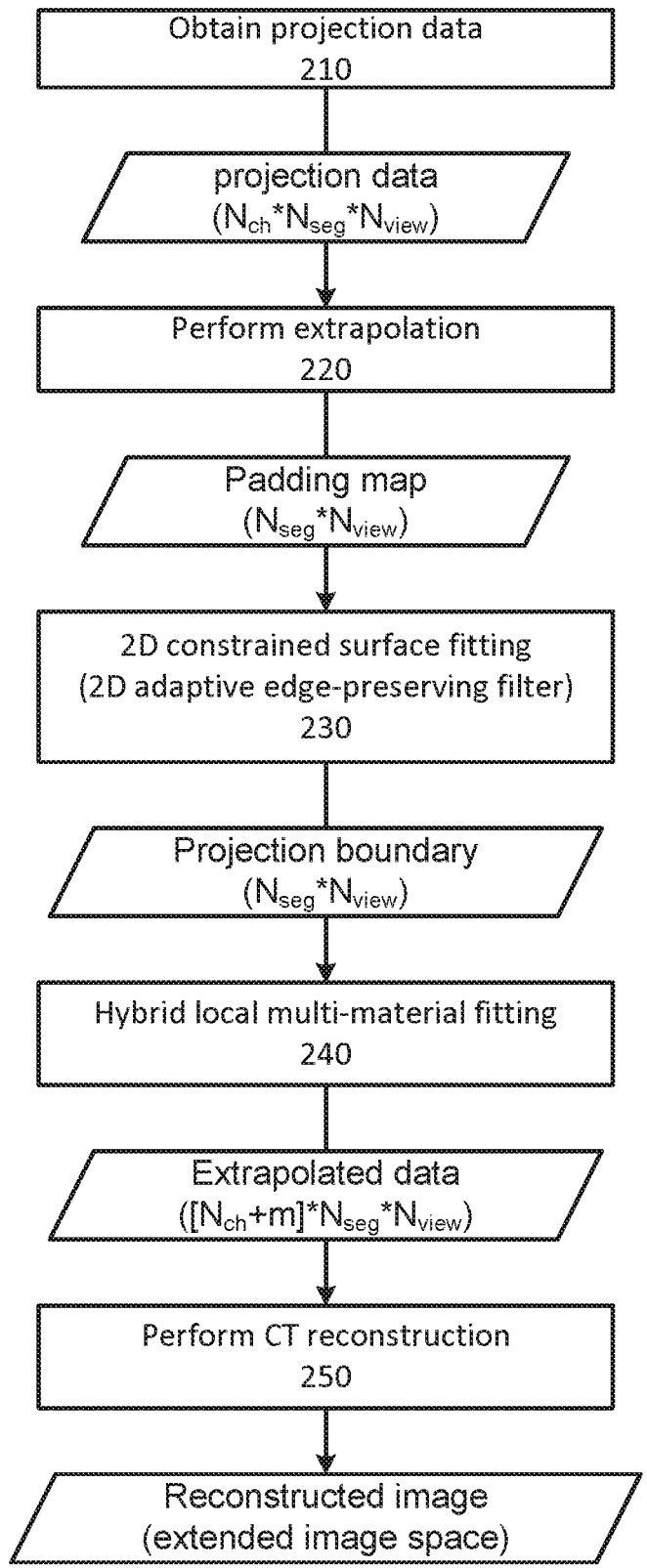
FIG. 5 shows a flow diagram of an extrapolation method to fill a truncation region in projection data, according to one implementation.

FIG. 5 shows a flow diagram of method 200 for extending projection data into a truncation region, which is a non-limiting example of the methods described herein. In certain implementations, method 200 can be used to preform a first order smoothed hybrid local multi-materials fitting method (SHLMMF) to correct truncation by first using projections to detect an outer boundary in the truncation rejoin to which projection data are to be extrapolated. Then, attenuation values can be filled/extrapolated in the truncation region using a hybrid fitting method that is performed using the projections near truncation region and boundary information to fill the missing data. In certain implementations, the hybrid fitting function can include a water cylinder fitting term and a polynomial fitting term for local peaks. Additionally, in certain implementations, the hybrid fitting function can include a water cylinder fitting term that is fit to the major water type of tissues, and the polynomial term is fit to other tissue type (e.g., bone). This method is more accurate and robust than other fitting methods that have been previously used. After extending the projection data to fill in the missing projection data in the truncation region, the extended projection data can then be used to reconstruct an image.

In step 210 of method 200, the projection data is obtained. This projection data can be obtained by performing a CT scan using a CT scanner such as the CT scanner described herein. Also, the projection data can be obtained by recalling from computer memory projection data that has been previously obtained.

In one non-limiting example, the projection data is collected with a C-arm system, with an X-ray source and a flat-panel detector mounted onto the opposing ends of the C-arm. The FOV might be too small or offset from the object OBJ such that the FOV fails to span the object OBJ for at least some views, leading to truncation artifacts in clinical images, as discussed above. Such artifacts may obscure low-contrast soft-tissue anatomy in the applications of clinical interest (e.g., intracranial hemorrhages might be obscured by the truncation artifacts even after scatter correction and beam-hardening corrections are performed).

Each of the steps of method 200 produces a result, which is shown in a data box below the respective step. For step 210 the resultant output is the projection data for which part of the attenuation information has been truncated in at least some views, as shown in FIG. 4A. The number of detector channels is $N_{ch}$. Similarly, $N_{seg}$ is the number of detector rows; and $N_{view}$ is the number of projection views.

Figure 6:
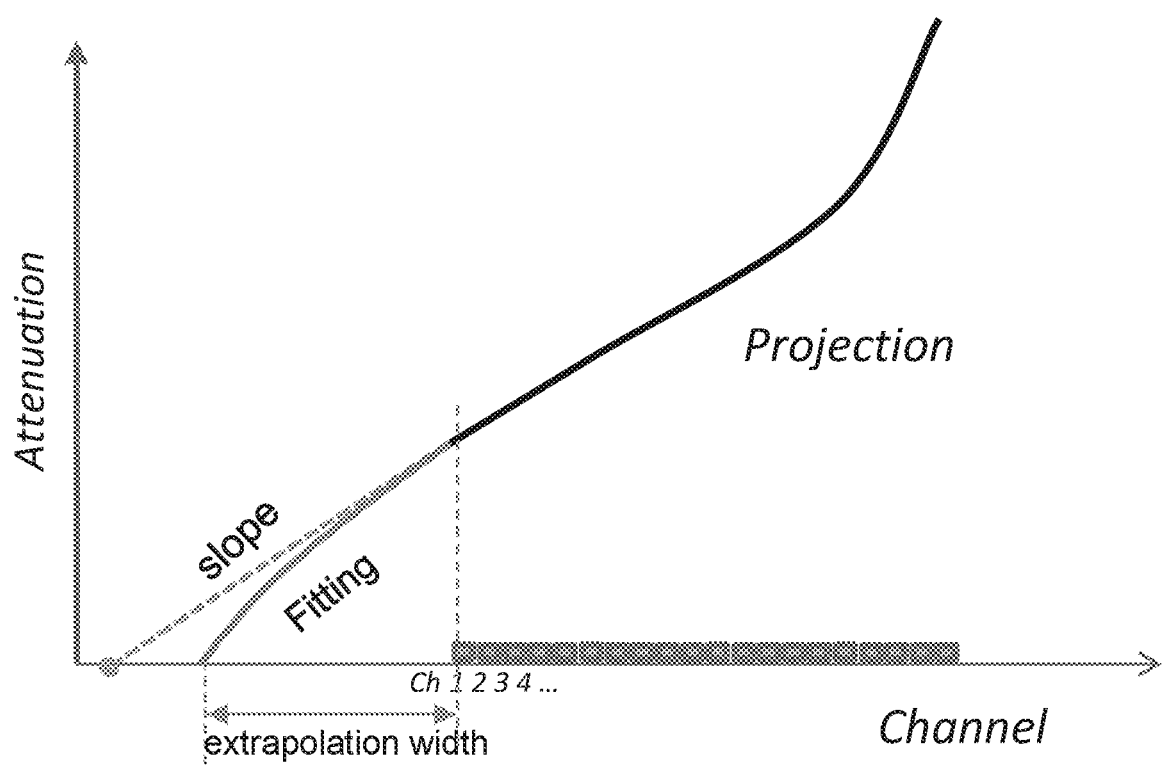
FIG. 6 shows a plot of fitting to determine an extrapolation width, according to one implementation.

In step 220 of method 200, an initial extrapolation is performed. The extrapolation can use any known method. For example, the initial extrapolation can be performed using any of the first four methods in Table 1. In certain implementations, the initial extrapolation is performed as illustrated in FIG. 6.

For example, for each row the detector in a view, the detector channels of projection data (referred to as segments) nearest the truncation are curve fit by a line. Then, for each truncated boundary of the projection data, the sloped of the curve fit line can be used with a water-cylinder fitting method or other extrapolation method to obtain an extrapolation width. The combination of extrapolation widths for all of the rows makes up a padding map (also called a padding-channel map) that is a two-dimensional function of the rows and views. The padding map can have jagged profile in both the row and view directions. Thus, if method 200 were to skip directly from step 220 to step 250 and reconstruct an image based on the initial extrapolation, then method 200 would produce results similar to the first four methods in Table 1. But method 200 does not skip steps 230 and 240.

Also, the result from step 220 is the padding map based on the extrapolation widths. Thus, a complete extrapolation is not required, and simply determining the zero crossing for the extrapolation curve is sufficient for determining the respective extrapolation widths for each of the rows and views.

In step 230 of method 200, the jagged profile of the padding map is smoothed. In certain implementations, this smoothing is achieved using a two-dimensional constrained surface fitting, and, in other implementations, the smoothing is achieved using a two-dimensional edge preserving filter. Further variations of the method of smoothing the padding map can be implemented without departing from the spirit or essential characteristics thereof, as will be understood by those skilled in the art.

Figure 7A:
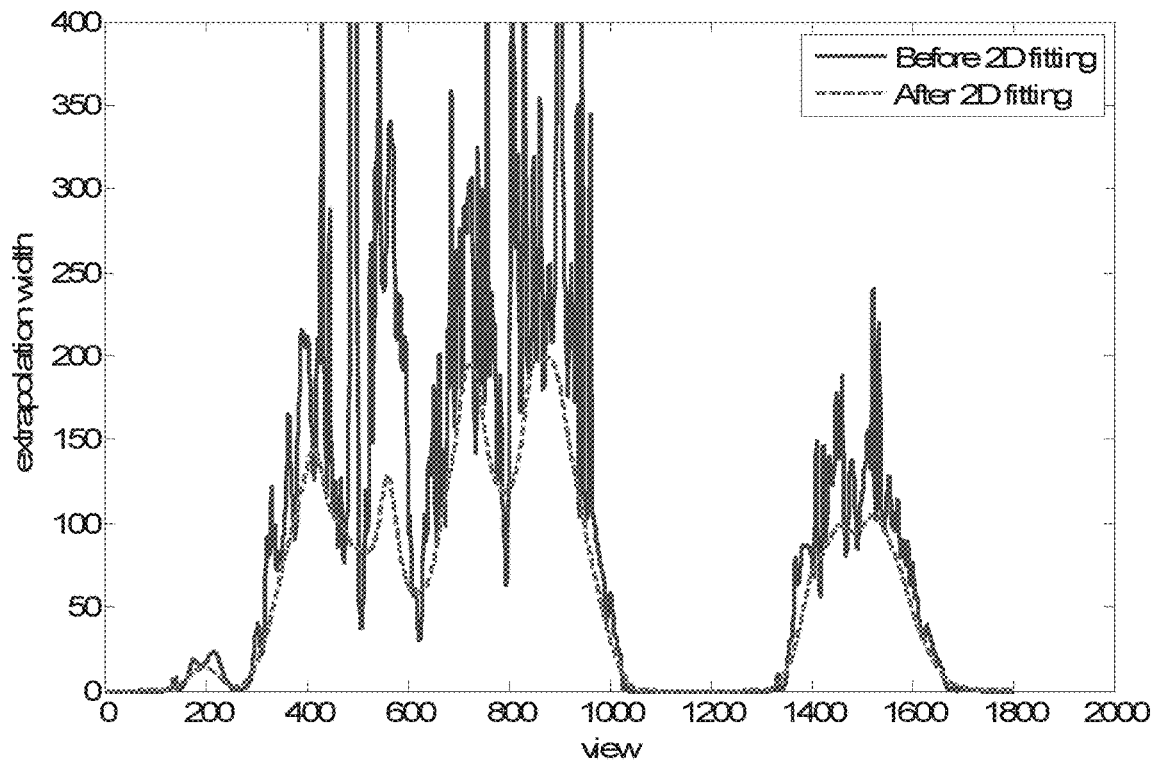
FIG. 7A shows a plot of fitting a padding map along a lineout in the view direction, according to one implementation.
Figure 7B:
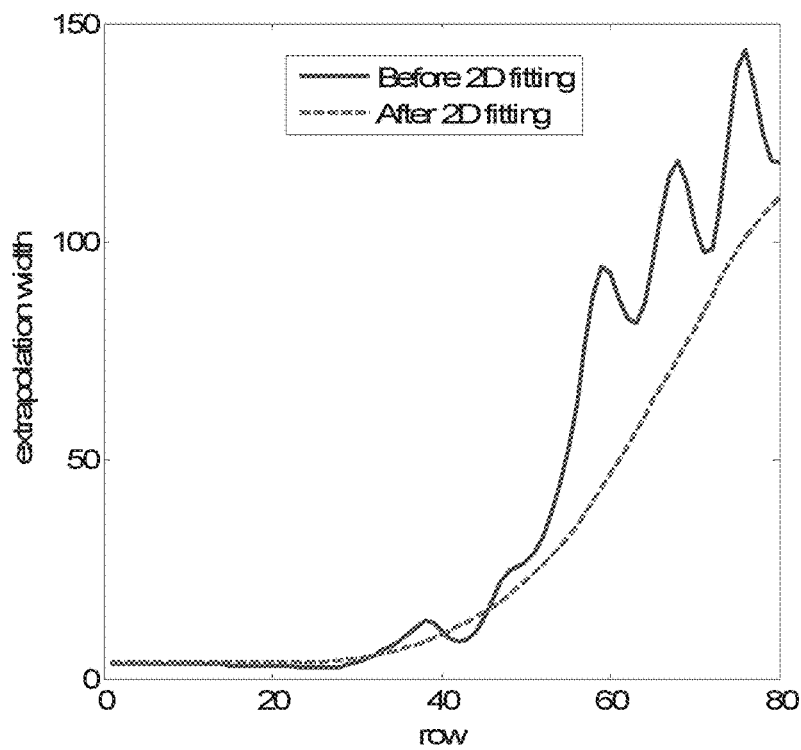
FIG. 7B shows a plot of fitting the padding map along a lineout in the row direction, according to one implementation.

For example, FIGS. 7A and 7B show respective lineouts of a padding map. In FIG. 7A, the lineout is a function of the view index for a constant row index. And in FIG. 7B, the lineout is a function of the row index with the view index held constant. In both figures, the solid line is the padding map before fitting, and the dashed line is the padding map after fitting. Fitting the padding map suppresses the noise and tissue-type effects discussed above. Empirical observations indicate that smaller extrapolation widths tend to be more accurate and reliable, and errors in which noise or other factors result in extrapolation widths significantly diverging from a physically intuitive value tend to happen more frequently by the extrapolation widths becoming too large rather than too small. That is, intuitively adjacent extrapolation widths are anticipated to be approximately equal, such that, when two adjacent extrapolation widths disagree significantly, the smaller of the two is likely the more reliable. This insight/heuristic can be incorporated into the analysis by including a weight w that is a function of the extrapolation widths and/or other indicia of the trustworthiness of the respective extrapolation widths (e.g., a signal to noise ratio for the segments of the projection data used in determining a given extrapolation width).

In implementations using a two-dimensional adaptive edge-preserving filter, the two-dimensional adaptive edge-preserving filter, such as a non-linear diffusion filter, is applied on padding map m. For example, the edge-preserving filter can preserve or otherwise give preferred status to smaller values of the extrapolation widths in the padding map by using a weighting w that is a function of the extrapolation widths. That is, rows with smaller extrapolation widths are considered more reliable, therefore, given more weight in determining a moving average (i.e., smaller extrapolation widths have more contribution to filter). This result can be achieved, e.g., by smoothing/fitting the padding map m using the equation $m' = \text{conv2}(wm, f)/\text{conv2}(w, f)$, wherein $f$ is a 2 dimensional filter, and conv2 is two-dimensional convolution.

In implementations using a two-dimensional constrained surface to smooth/fit the padding map m, the preferred status of smaller extrapolation widths can also be realized by giving larger weights to rows with smaller extrapolation widths value.

Regardless of the implementation, the result of step 230 is a smoothed/fitted padding map that is used as the extrapolation width of the truncated projections for the final extrapolation in step 240 (i.e., the smoothed/fitted padding map is the boundary for the projection data after extrapolating the extended/virtual projection data to fill the truncation region).

In step 240 of method 200, the updated padding map m' is used as the width of the truncation regions of the respective rows to be filled through extrapolation based on the segments of the measured projection data that are at or near the truncation boundary. Given the constraints imposed by the extrapolation width and matching the characteristics of the projection data near the boundary (e g, boundary conditions of the magnitude, slope, and curvature), the coefficients of the extrapolation methods listed below can be uniquely determined.

In certain implementations, the fitting method can use a water cylinder fitting method. That is, the fitting method can use a function $f$ that includes a water cylinder fitting function $f_w$. Accordingly, for each row, the respective extrapolation width from the updated padding map m' can be used in combination with boundary conditions based on the edge segment(s) of the row (and in certain implementations a windowed average with adjacent rows in the view) to parameterize a water-cylinder fitting function, which is given by $f_w = 2\mu_w \sqrt{R^2 - Ch^2}$ wherein R is the radius of fitted cylinder, and Ch is the distance of the padded channel to origin of the cylinder.

As discussed above, the water-cylinder approximation starts to fail when the truncation region is not shallow. The water-cylinder approximation is based on the hypothesis that truncation region are predominantly made up of materials consisting of water or exhibiting X-ray attenuation similar to water and having a shape that is approximately cylindrical. This hypothesis can be sound when the truncation region is, e.g., the soft-tissue portion of a shoulder, but begins to fail when the truncation region includes bone or other materials that differ from water, are not cylindrical in shape or are inhomogeneous. Thus, it is not uncommon for circumstances to depart from the water-cylinder ideal. Accordingly, when other types of tissue are present in the truncation regions, a different extrapolation function is desired.

Figure 8:
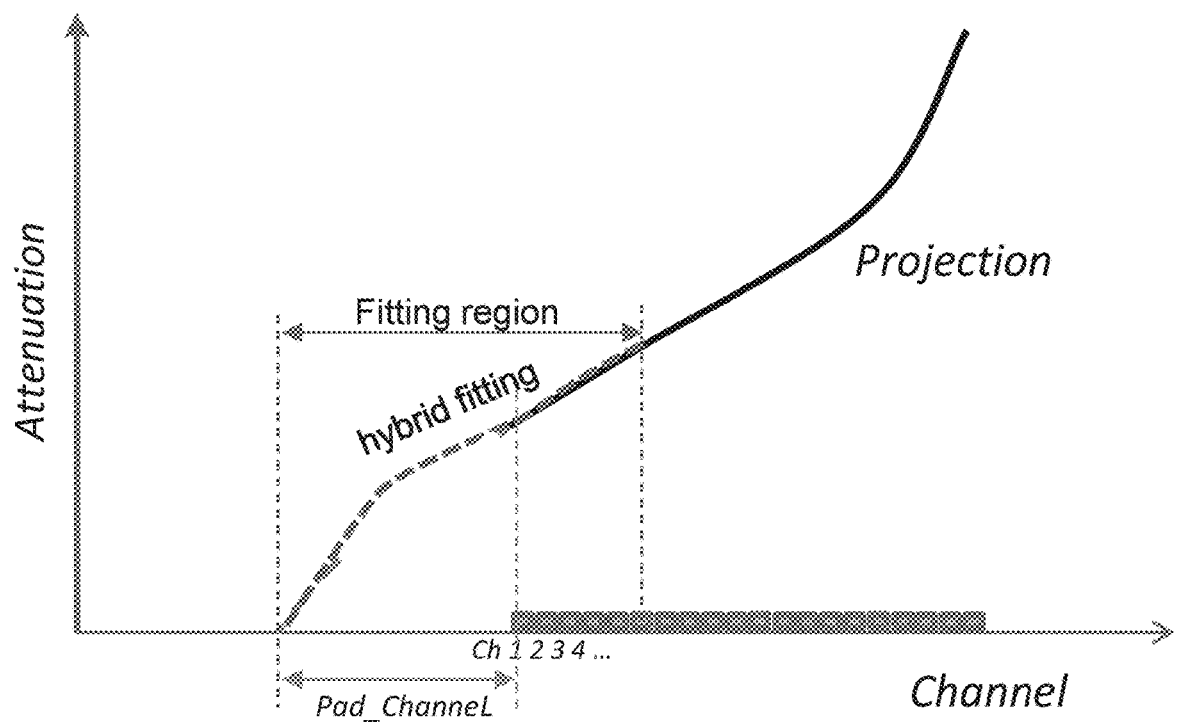
FIG. 8 shows a plot of a hybrid method for extrapolating to extend projection data into a truncation region, according to one implementation.

As discussed above, a different extrapolation function is desired especially when bone is in the truncated regions, which is common in cases of severe truncation. The bone will contribute a local peak on projection along channels, and the function $f_w$ does not fit the profile well. In these cases, another term can be added to the fitting function to fit the bone peak and improve the fitting. In certain implementations, a low order polynomial $f_p$ (e.g., a second order polynomial) can be added to the fitting function to fit the bone peak and improve the fitting. This combination of fitting functions is called a hybrid local multi-materials fitting, and it is illustrated in FIG. 8. In the hybrid local multi-materials fitting, the fitting function is given by $$f=af_w+bf_p,$$

wherein the second-order polynomial fitting function $f_p$ is given by $$f_p=c_0+c_1ch+c_2ch^2, \text{ and}$$

a, b are coefficients and optimized during fitting as well as coefficients $c_0$, $c_1$, and $c_2$ in the polynomial fitting function $f_p$. To avoid an underdetermined fitting of the coefficients, more pixel values can be used from the measured projection data nearest to the truncation region. Further, the number of measured projection data values can exceed the number of coefficients with being overdetermined by, e.g., fitting the data in a least squares sense or according to some other distance measure or objective function to be minimized. This also mitigates issues arising from fitting to noisy data. The optimal fit can be searched out and determined, e.g., using a gradient descent method or any other known optimization or constrained optimization method.

In certain implementations, the hybrid local multi-materials fitting model can be further refined to include a fitting function for a third type of materials (e.g., a muscle fitting function $f_m$, and the fitting function can be given by $$f=af_w+bf_m+cf_p,$$

wherein $f_m$ is a local muscle fitting term and a, b, and c are coefficients that are optimized during fitting.

The result of step 240 is projection data that has been extended to include the truncation region, which has been filled in using the above-discussed extrapolation methods.

In step 250, the extended projection data is used to reconstruct a three-dimensional image of the object OBJ. Any known reconstruction method can be used.

Figure 9A:
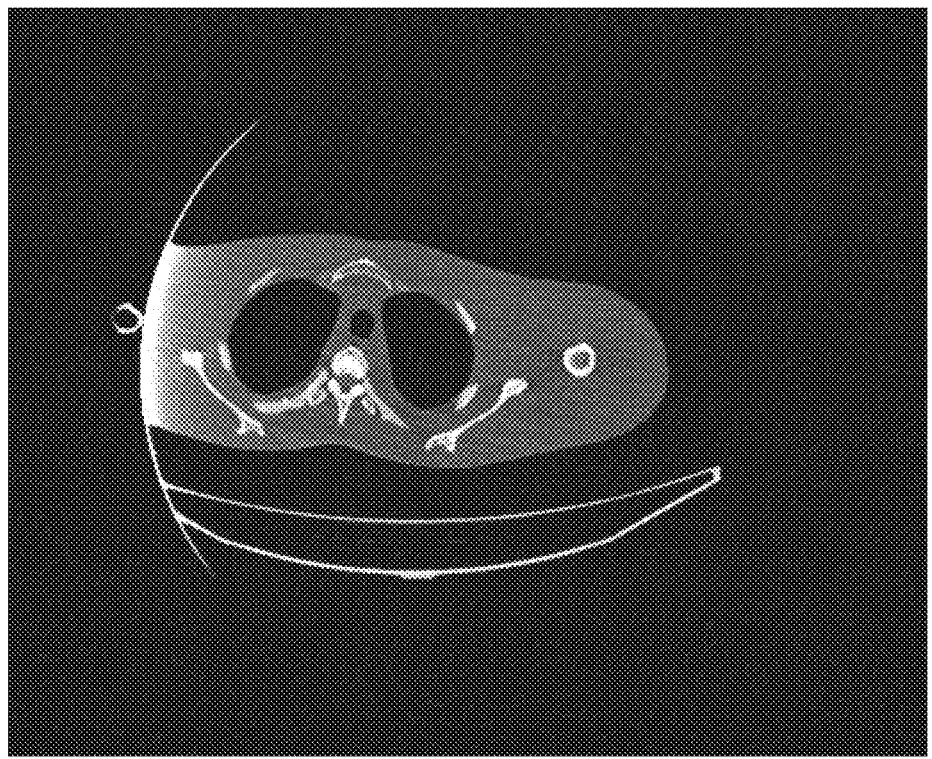
FIG. 9A shows an axial view of a reconstructed image generated using zero padding in the truncation region, according to one implementation.
Figure 9B:
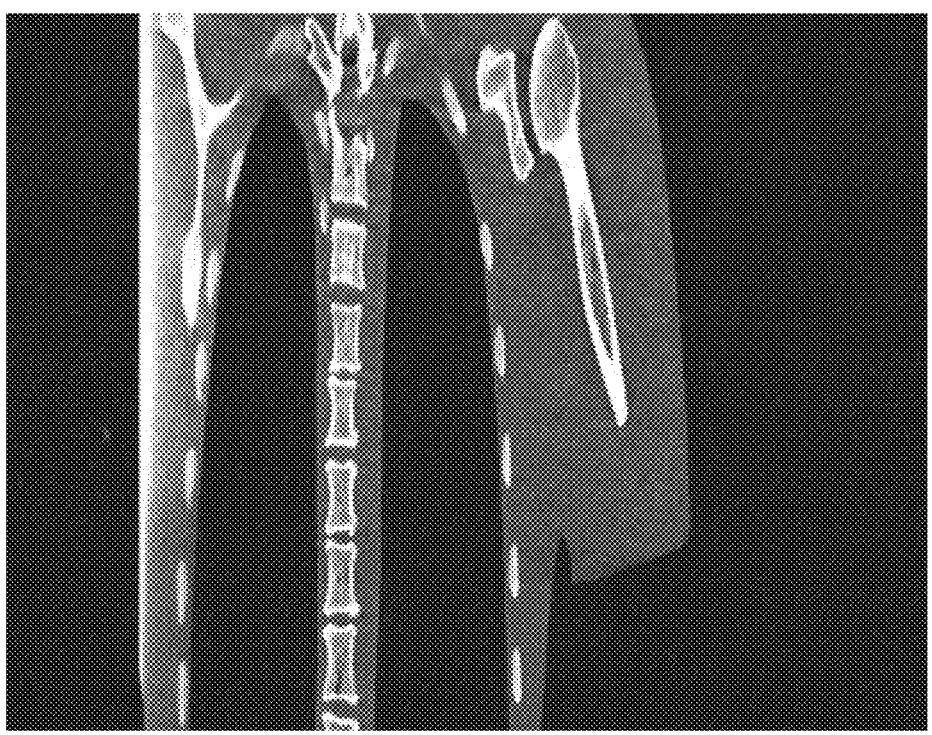
FIG. 9B shows a coronary view of a reconstructed image generated using zero padding in the truncation region, according to one implementation.
Figure 10A:
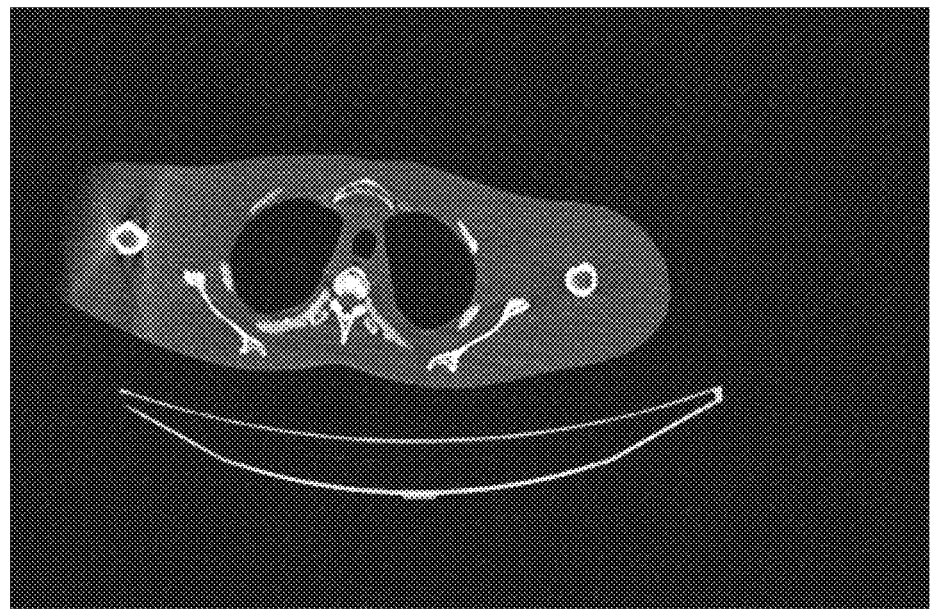
FIG. 10A shows an axial view of a reconstructed image generated using method 200 described herein to fill the truncation region, according to one implementation.
Figure 10B:
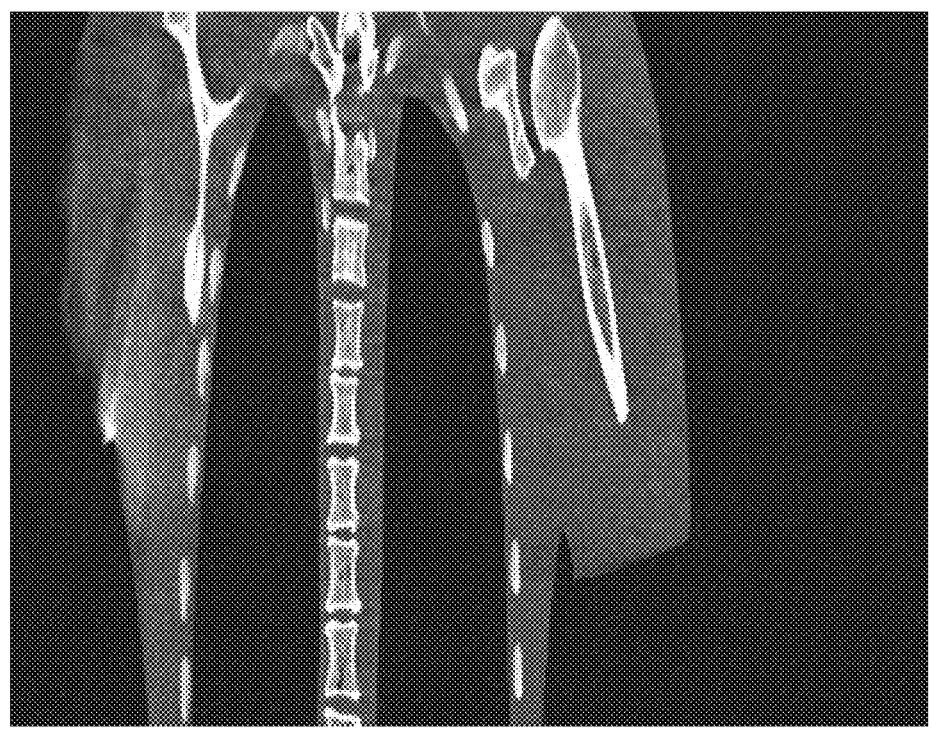
FIG. 10B shows a coronary view of a reconstructed image generated using method 200 described herein to fill the truncation region, according to one implementation.

The improvement enabled by method 200 is illustrated by comparing FIGS. 9A and 9B, which are multi-planar reconstructions (MPRs) for an axial view and a coronary view respectively of a reconstructed image generated using zero padding, with FIGS. 10A and 10B, which are corresponding MPRs generated using method 200. It can be readily observed that method 200 represents a marked improvement over zero padding.

The methods described herein have several advantages over conventional methods. For example, smoothing/fitting the padding map is improved by the insight that in general smaller extrapolation widths tend to be more accurate and trustworthy. Thus, smoothing/fitting the padding map can be performed by a two-dimensional constrained surface fitting or two-dimensional adaptive edge-preserving filter, which are weighted to favor smaller extrapolation widths to improve the accuracy of the updated padding map. More generally, the smoothing/fitting of the padding map has advantageous effect of reducing jagged edges.

Additionally, method 200 applies a hybrid local multi-material fitting method instead of a pure water-cylinder fitting method. This improved fitting method provides a better approximation to actual clinical applications when other materials are present in the truncated region, such as bone. Thus, more accurate fitting can be achieved.

Figure 11:
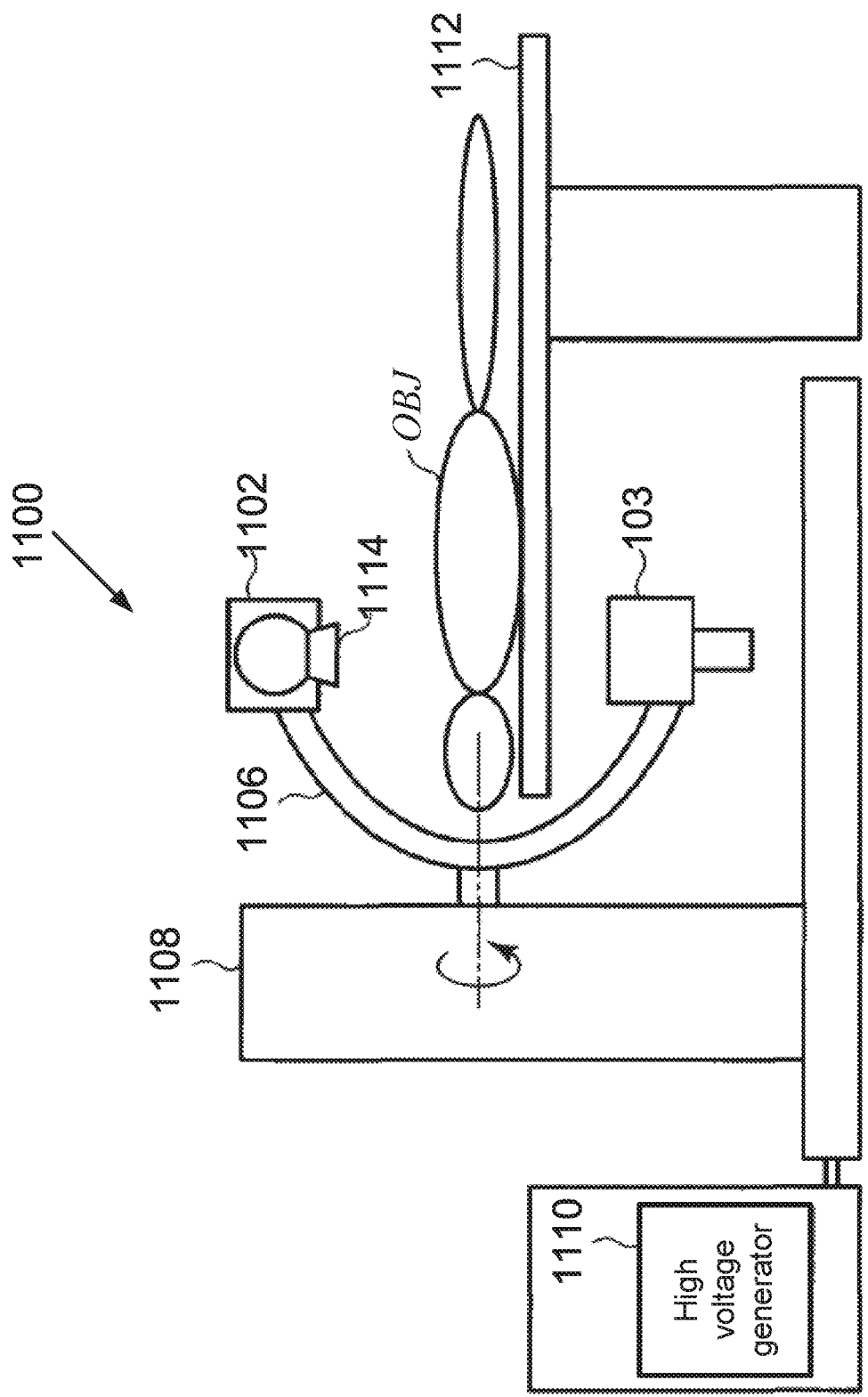
FIG. 11 shows a diagram of a CT scanner, according to one implementation.

FIG. 11 shows an example of a CT apparatus using a C-arm configuration. As shown in FIG. 11, the CT apparatus 1100 includes an X-ray source 112, X-ray detector 103, C-arm 1106, stand 1108, high-voltage generator 1110, bed 1112, and X-ray stop device 1114.

The high-voltage generator 1110 generates a high voltage to be applied between the electrodes of the X-ray source 112, and also generates a filament current to be supplied to the cathode filament of the X-ray source 112. Upon receiving the high voltage and filament current, the X-ray source 112 generates X-rays. The X-ray stop device 1114 shapes X-rays generated by the X-ray source 112. The X-ray detector 103 can be a two-dimensional array of a plurality of detection elements (pixels) that directly or indirectly convert incident X-rays into electric charges. The X-ray source 112 is mounted on, for example, one end of the C-arm 1106. The X-ray detector 103 is mounted on the other end of the C-arm 1106. The X-ray detector 103 faces the X-ray source 112 through an object OBJ to be examined which is placed on the bed 1112. The C-arm 1106 is rotatably supported on the stand 1108. Repeating radiography with respect to the object OBJ while rotating the C-arm 1106 makes it possible to acquire X-ray frames (projection data) in many directions which are required for three-dimensional image reconstruction.

Radiography control circuitry controls the rotation of the C-arm 1106, the application of high voltages from the high-voltage generator 1110 to the X-ray source 112, and reading of signals from the X-ray detector 103 in order to execute rotational radiography and generate X-ray projection data. Although FIG. 11 does not show processing circuitry to perform the steps of method 200, the reconstruction of a CT image according to the methods described herein can be performed using similar processing circuitry (e.g., a CPU) to what is described below with reference to FIG. 12.

Figure 12:
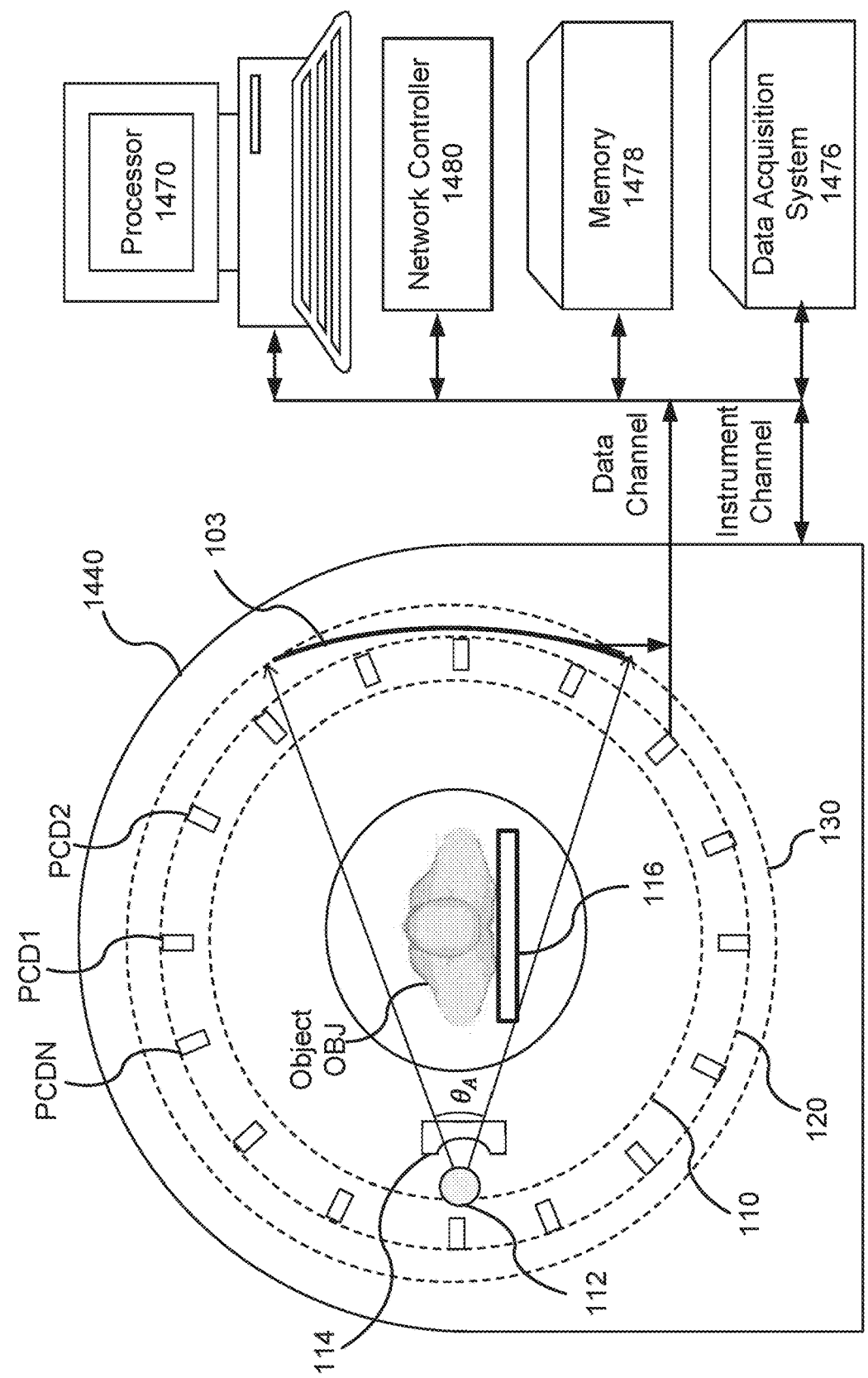
FIG. 12 shows a diagram of a C-arm CT scanner, according to one implementation.

FIG. 12 shows a computed tomography (CT) scanner having both energy-integrating detectors arranged in a third-generation geometry and PCDs arranged in a fourth-generation geometry. Illustrated in FIG. 12 is an implementation for placing the PCDs in a predetermined fourth-generation geometry in combination with a detector unit 103 in a predetermined third-generation geometry in a CT scanner system. The diagram illustrates relative positions among the X-ray source 112, the collimator/filter 114, the X-ray detector 103, and the photon-counting detectors PCD1 through PCDN.

In addition to the configuration of the X-ray source 112 and the detectors including the detector unit 103 and the PCDS show in FIG. 12, other types and combinations of X-ray detectors and X-ray source can be used to obtain the projection data. For example, either the detector unit 103 or the PCDS could be omitted from the scanner shown in FIG.

12 and the scanner could still obtain projection data, albeit different from the projection data obtained using the complete system shown in FIG. 12. Further, kV switching could be used with energy-integrating detectors or PCDs. In certain implementations, the PCDS can be direct X-ray detectors using semiconductors to convert the X-rays directly to photoelectrons without first generating scintillation photons. Additionally, in certain implementations, a broadband X-ray source can be used with spectrally-resolving X-ray detectors. These spectrally-resolving X-ray detectors can include PCDs in any configurations (e.g., a predetermined third-generation geometry or a predetermined fourth-generation geometry) or energy-integrating detectors preceded by respective spectral filters. In certain implementations, the X-ray source can include multiple narrow-band X-ray sources, such as in a dual source CT scanner. In general, any known combination of detector type and configuration together with any known type or combination of X-ray sources can be used to generate the projection data.

Returning to FIG. 12, FIG. 12 also shows circuitry and hardware for acquiring, storing, processing, and distributing X-ray projection data. The circuitry and hardware include: a processor 1470, a network controller 1480, a memory 1478, and a data acquisition system 1476.

In one alternative implementation, the CT scanner includes PCDs but does not include the energy-integrating detector unit 103.

As the X-ray source 112 and the detector unit 103 are housed in a gantry 1440 and rotate around circular paths 110 and 130 respectively, the photon-counting detectors PCDs and the detector unit 103 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 103 continuously detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112, the PCDs and the detector unit 103 collectively form three predetermined circular paths that differ in radius. At least one X-ray source 112 rotates along a first circular path 110 while the photon-counting detectors are sparsely placed along a second circular path 120. Further, the detector unit 103 travels along a third circular path 130. The first circular path 110, second circular path 120, and third circular path 130 can be determined by annular rings that are rotatably mounted to the gantry 1440.

Additionally, alternative embodiments can be used for placing the photon-counting detectors in a predetermined fourth-generation geometry in combination with the detector unit in a predetermined third-generation geometry in the CT scanner.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 103 to a data acquisition system 1476, a processor 1470, memory 1478, network controller 1480. The data acquisition system 1476 controls the acquisition, digitization, and routing of projection data from the detectors. The data acquisition system 1476 also includes radiography control circuitry to control the rotation of the annular rotating frames 110 and 130. In one implementation data acquisition system 1476 will also control the movement of the bed 116, the operation of the X-ray source 112, and the operation of the X-ray detectors 103. The data acquisition system 1476 can be a centralized system or alternatively it can be a distributed system. In an implementation, the data acquisition system 1476 is integrated with the processor 1470. The processor 1470 performs functions including reconstructing images from the projection data, pre-reconstruction processing of the projection data, and post-reconstruction processing of the image data. The processor 1470 also performs the functions and methods described herein.

The pre-reconstruction processing of the projection data can include correcting for detector calibrations, detector nonlinearities, polar effects, noise balancing, and material decomposition. Additionally, the pre-reconstruction processing can include preforming extrapolation to extend the projection data into truncation regions using various steps of method 200.

Post-reconstruction processing can include filtering and smoothing the image, volume rendering processing, and image difference processing as needed.

The image-reconstruction process can be performed using filtered back-projection, iterative-image-reconstruction methods, or stochastic-image-reconstruction methods. Additionally, the image-reconstruction processing can include a combined process of reconstructing and denoising the reconstructed images using various steps of method 200 (e.g., step 250).

Both the processor 1470 and the data acquisition system 1476 can make use of the memory 1476 to store, e.g., projection data, reconstructed images, calibration data and parameters, and computer programs.

The processor 1470 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 1478 can be a hard disk drive, CD-ROM drive, DVD drive, FLASH drive, RAM, ROM or any other electronic storage known in the art.

The network controller 1480, such as an Intel Ethernet PRO network interface card from Intel Corporation of America, can interface between the various parts of the CT scanner. Additionally, the network controller 1480 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) imaging apparatus to reduce artifacts in reconstructed CT images, the apparatus comprising:
processing circuitry configured to
obtain projection data representing an intensity of radiation detected at a plurality of detector elements having an axial and a trans-axial direction, the radiation having been transmitted through an object to be imaged, and in one or more views represented in the projection data a part of the object is outside of a field of view of the radiation detected by the plurality of detector elements,
determine extrapolation widths for extending the projection data corresponding to the one or more views by filling a truncation region extrapolated from the projection data,
smooth the extrapolation widths by decreasing differences between extrapolation widths that are adjacent in the axial direction and by decreasing differences between extrapolation widths that are adjacent in a view direction,
extrapolate, using the smoothed extrapolation widths, extended projection data to fill truncation regions and generate non-truncated projection data, and
reconstruct an image from the non-truncated projection data.

2. The apparatus according to claim 1, wherein the processing circuitry is further configured to extrapolate the extended projection data using a hybrid material fit that represents a weighted combination of material models of two or more materials.

3. The apparatus according to claim 2, wherein the processing circuitry is further configured to extrapolate the extended projection data using the hybrid material fit that includes two or more of a water material model, a bone material model, and a muscle material model.

4. The apparatus according to claim 3, wherein the processing circuitry is further configured to extrapolate the extended projection data using the hybrid material fit that uses the water material model, wherein the water material model uses a cylindrical shape to approximate attenuation in the truncation region.

5. The apparatus according to claim 1, wherein the processing circuitry is further configured to smooth the extrapolation widths by one of a constrained surface fitting method and a filtering or convolution method.

6. The apparatus according to claim 5, wherein the processing circuitry is further configured to smooth the extrapolation widths using the filtering or convolution method, wherein the filtering or convolution method uses an adaptive edge-preserving filter that is weighted to bias a filter result towards extrapolation widths having smaller values.

7. The apparatus according to claim 1, wherein the processing circuitry is further configured to smooth the extrapolation widths with a bias to increase a contribution of extrapolation widths having smaller values relative to a contribution of extrapolation widths having larger values.

8. A computed tomography (CT) scanner, comprising:
a support member,
a rotating member configured rotatably in the support member, the rotating member including
an X-ray source configured to emit X-rays,
an X-ray detector arranged on the rotating member diametrically opposed to the X-ray source and configured to detect, using a plurality of detector elements, the X-rays emitted to generate projection data representing an intensity of the X-rays detected at the plurality of detector elements, the plurality of detector elements having an axial and a trans-axial direction, and
a space provided between the X-ray source and the X-ray detector to accommodate an object to be imaged, which is at least partially within a an image volume within which an image is to be reconstructed from the projection data, and in one or more views represented in the projection data a part of the object is outside of a field of view of the radiation detected by the plurality of detector elements; and processing circuitry configured to
   determine extrapolation widths for extending the projection data corresponding to the one or more views by filling a truncation region extrapolated from the projection data,
   smooth the extrapolation widths by decreasing differences between extrapolation widths that are adjacent in the axial direction and by decreasing differences between extrapolation widths that are adjacent in a view direction,
   extrapolate, using the smoothed extrapolation widths, extended projection data to fill truncation regions and generate non-truncated projection data, and
   reconstruct an image from the non-truncated projection data.

9. The CT scanner according to claim 8, wherein the rotating member is one of a C-arm and an annular ring, and the X-ray source is further configured to emit X-rays in a shape of a cone beam.

10. The CT scanner according to claim 8, wherein
   the processing circuitry is further configured to extrapolate the extended projection data using a hybrid material fit that represents a weighted combination of material models of two or more materials, and
   the hybrid material fit includes two or more of a water material model, a bone material model, and a muscle material model.

11. The CT scanner according to claim 8, wherein the processing circuitry is further configured to smooth the extrapolation widths by one of a constrained surface fitting method and a filtering or convolution method.

12. The CT scanner according to claim 8, wherein the processing circuitry is further configured to smooth the extrapolation widths with a bias to increase a contribution of extrapolation widths having smaller values relative to a contribution of extrapolation widths having larger values.

13. A method, comprising:
   obtaining projection data representing an intensity of radiation detected at a plurality of detector elements having an axial and a trans-axial direction, the radiation having been transmitted through an object to be imaged, and in one or more views represented in the projection data a part of the object is outside of a field of view of the radiation detected by the plurality of detector elements,
   determining extrapolation widths for extending the projection data corresponding to the one or more views by filling a truncation region extrapolated from the projection data,
   smoothing the extrapolation widths by decreasing differences between extrapolation widths that are adjacent in the axial direction and by decreasing differences between extrapolation widths that are adjacent in a view direction,
   extrapolating, using the smoothed extrapolation widths, extended projection data to fill truncation regions and generate non-truncated projection data, and
   reconstructing an image from the non-truncated projection data.

14. The method according to claim 13, wherein the step of extrapolating the extended projection data is performed using a hybrid material fit that represents a weighted combination of material models of two or more materials.

15. The method according to claim 14, wherein the step of extrapolating the extended projection data is performed using the hybrid material fit that includes two or more of a water material model, a bone material model, and a muscle material model.

16. The method according to claim 13, wherein the step of extrapolating the extended projection data is performed by extrapolating the extended projection data using the hybrid material fit that uses the water material model, wherein the water material model uses a cylindrical shape to approximate attenuation in the truncation region.

17. The method according to claim 13, wherein the step of smoothing the extrapolation widths is performed using one of a constrained surface fitting method and a filtering or convolution method.

18. The method according to claim 17, wherein the step of smoothing the extrapolation widths is performed using the filtering or convolution method, wherein the filtering or convolution method uses an adaptive edge-preserving filter that is weighted to bias a filter result towards extrapolation widths having smaller values.

19. The method according to claim 18, wherein the step of smoothing the extrapolation widths is performed by biasing a process of smoothing the extrapolation widths to increase a contribution of extrapolation widths having smaller values relative to a contribution of extrapolation widths having larger values.

20. A non-transitory computer-readable medium storing executable instructions, wherein the instructions, when executed by processing circuitry, cause the processing circuitry to perform the CT imaging method according to claim 13.

* * * * *